(12) United States Patent
Douk et al.

(10) Patent No.: US 8,372,133 B2
(45) Date of Patent: Feb. 12, 2013

(54) POLYMERIC IMPLANT DELIVERY SYSTEM

(75) Inventors: Nareak Douk, Lowell, MA (US); Rany Busold, Charlestown, MA (US); Lee Core, Cambridge, MA (US); Kicherl Ho, Acton, MA (US); My Le, Pawtucket, RI (US)

(73) Assignee: 480 Biomedical, Inc., Watertown, MA (US)

( * ) Notice: Subject to any disclaimer, the term of this patent is extended or adjusted under 35 U.S.C. 154(b) by 216 days.

(21) Appl. No.: 12/573,687

(22) Filed: Oct. 5, 2009

(65) Prior Publication Data

US 2011/0082464 A1 Apr. 7, 2011

(51) Int. Cl.
*A61F 2/06* (2006.01)
(52) U.S. Cl. ...................... 623/1.12; 623/903
(58) Field of Classification Search .......... 623/1.11, 623/1.12, 903; 606/108, 159, 198, 200, 213, 606/151, 215, 194; 128/831, 843
See application file for complete search history.

(56) References Cited

U.S. PATENT DOCUMENTS

| | | | | |
|---|---|---|---|---|
| 5,011,488 A * | 4/1991 | Ginsburg | | 606/159 |
| 5,356,423 A | 10/1994 | Tihon | | |
| 5,516,781 A | 5/1996 | Morris | | |
| 5,562,725 A | 10/1996 | Schmitt | | |
| 5,563,146 A | 10/1996 | Morris | | |
| 5,571,135 A * | 11/1996 | Fraser et al. | | 623/1.12 |
| 5,616,608 A | 4/1997 | Kinsella | | |
| 5,650,447 A | 7/1997 | Keefer | | |
| 5,665,077 A | 9/1997 | Rosen | | |
| 5,665,728 A | 9/1997 | Morris | | |
| 5,676,963 A | 10/1997 | Keefer | | |
| 5,716,981 A | 2/1998 | Hunter | | |
| 5,733,925 A | 3/1998 | Kunz | | |
| 5,741,325 A | 4/1998 | Chaikof | | |
| 5,749,921 A * | 5/1998 | Lenker et al. | | 623/1.42 |
| 5,762,625 A | 6/1998 | Igaki | | |
| 5,766,710 A | 6/1998 | Turnlund | | |
| 5,788,979 A | 8/1998 | Alt et al. | | |
| 5,824,053 A | 10/1998 | Khosravi | | |
| 5,851,217 A | 12/1998 | Wolff | | |
| 5,871,535 A | 2/1999 | Wolff | | |
| 5,899,935 A | 5/1999 | Ding | | |
| 5,968,091 A | 10/1999 | Pinchuk et al. | | |
| 5,976,153 A * | 11/1999 | Fischell et al. | | 623/1.11 |

(Continued)

FOREIGN PATENT DOCUMENTS

| | | |
|---|---|---|
| EP | 0724436 B1 | 1/2004 |
| EP | 1400218 | 3/2004 |

(Continued)

OTHER PUBLICATIONS

Hietala et al., Thrombosis and Haemostatis, vol. 92, No. 6 2004, "Platelet deposition on stainless steel, spiral, and braided polylactide stents", pp. 1394-1401.

*Primary Examiner* — Elizabeth Houston
(74) *Attorney, Agent, or Firm* — Bingham McCutchen LLP

(57) ABSTRACT

Delivery systems for a polymeric tubular implant, kits that include such delivery systems, and methods of treating patients by implanting tubular implants using the delivery systems. The delivery systems include an inner shaft, an expandable member slidably disposed about the inner shaft and configured to receive the tubular implant, and a tubular outer shaft disposed about the inner shaft.

11 Claims, 5 Drawing Sheets

U.S. PATENT DOCUMENTS

| | | | |
|---|---|---|---|
| 5,984,957 | A | 11/1999 | Laptewicz |
| 5,994,444 | A | 11/1999 | Trescony |
| 5,997,468 | A | 12/1999 | Wolff et al. |
| 6,004,346 | A | 12/1999 | Wolff et al. |
| 6,005,020 | A | 12/1999 | Loomis |
| 6,051,021 | A | 4/2000 | Frid |
| 6,074,659 | A | 6/2000 | Kunz |
| 6,083,257 | A | 7/2000 | Taylor |
| 6,087,479 | A | 7/2000 | Stamler |
| 6,120,536 | A | 9/2000 | Ding |
| 6,161,399 | A | 12/2000 | Jayaraman |
| 6,171,232 | B1 | 1/2001 | Papandreou |
| 6,171,609 | B1 | 1/2001 | Kunz |
| 6,193,746 | B1 | 2/2001 | Strecker |
| 6,206,868 | B1 * | 3/2001 | Parodi ............................ 604/500 |
| 6,221,100 | B1 | 4/2001 | Strecker |
| 6,232,434 | B1 | 5/2001 | Stamler |
| 6,240,978 | B1 | 6/2001 | Gianotti |
| 6,245,103 | B1 | 6/2001 | Stinson |
| 6,261,594 | B1 | 7/2001 | Smith |
| 6,268,390 | B1 | 7/2001 | Kunz |
| 6,270,779 | B1 | 8/2001 | Fitzhugh |
| 6,284,305 | B1 | 9/2001 | Ding |
| 6,295,714 | B1 | 10/2001 | Roychowdhury |
| 6,299,604 | B1 | 10/2001 | Ragheb |
| 6,299,636 | B1 | 10/2001 | Schmitt |
| 6,306,421 | B1 | 10/2001 | Kunz |
| 6,338,739 | B1 | 1/2002 | Datta |
| 6,342,068 | B1 | 1/2002 | Thompson |
| 6,368,346 | B1 | 4/2002 | Jadhav |
| 6,379,691 | B1 | 4/2002 | Tedeschi |
| 6,403,635 | B1 | 6/2002 | Kinsella |
| 6,403,759 | B2 | 6/2002 | Stamler |
| 6,419,694 | B1 | 7/2002 | Sandock |
| 6,423,092 | B2 | 7/2002 | Datta |
| 6,429,232 | B1 | 8/2002 | Kinsella |
| 6,451,337 | B1 | 9/2002 | Smith |
| 6,471,978 | B1 | 10/2002 | Stamler |
| 6,488,705 | B2 | 12/2002 | Schmitt |
| 6,488,951 | B2 | 12/2002 | Toone |
| 6,506,411 | B2 | 1/2003 | Hunter |
| 6,515,009 | B1 | 2/2003 | Kunz |
| 6,544,544 | B2 | 4/2003 | Hunter |
| 6,569,191 | B1 | 5/2003 | Hogan |
| 6,569,195 | B2 | 5/2003 | Yang |
| 6,585,764 | B2 | 7/2003 | Wright |
| 6,589,546 | B2 | 7/2003 | Kamath |
| 6,592,617 | B2 | 7/2003 | Thompson |
| 6,599,928 | B2 | 7/2003 | Kunz |
| 6,605,115 | B1 | 8/2003 | Cooke |
| 6,632,242 | B2 | 10/2003 | Igaki |
| 6,645,518 | B2 | 11/2003 | Tedeschi |
| 6,656,966 | B2 | 12/2003 | Garvey |
| 6,663,881 | B2 | 12/2003 | Kunz |
| 6,706,274 | B2 | 3/2004 | Herrmann |
| 6,719,934 | B2 | 4/2004 | Stinson |
| 6,730,064 | B2 | 5/2004 | Ragheb |
| 6,737,447 | B1 | 5/2004 | Smith |
| 6,753,454 | B1 | 6/2004 | Smith |
| 6,776,796 | B2 | 8/2004 | Falotico |
| 6,790,228 | B2 | 9/2004 | Hossainy |
| 6,808,536 | B2 | 10/2004 | Wright |
| 6,855,366 | B2 | 2/2005 | Smith |
| 6,869,973 | B2 | 3/2005 | Garvey |
| 6,875,840 | B2 | 4/2005 | Stack |
| 6,884,429 | B2 | 4/2005 | Koziak |
| 6,887,266 | B2 | 5/2005 | Williams et al. |
| 6,887,485 | B2 | 5/2005 | Fitzhugh |
| 6,908,622 | B2 | 6/2005 | Barry |
| 6,932,930 | B2 | 8/2005 | DeSimone et al. |
| 7,008,397 | B2 | 3/2006 | Tweden |
| 7,011,678 | B2 | 3/2006 | Tenerz |
| 7,029,495 | B2 | 4/2006 | Stinson |
| 7,066,951 | B2 * | 6/2006 | Chobotov .................... 623/1.12 |
| 7,070,615 | B1 | 7/2006 | Igaki |
| 7,087,709 | B2 | 8/2006 | Stamler |
| 7,141,061 | B2 | 11/2006 | Williams et al. |
| 7,163,554 | B2 | 1/2007 | Williams et al. |
| 7,217,286 | B2 | 5/2007 | Falotico |
| 7,223,286 | B2 | 5/2007 | Wright |
| 7,229,473 | B2 | 6/2007 | Falotico |
| 7,279,175 | B2 | 10/2007 | Chen |
| 7,285,287 | B2 | 10/2007 | Williams et al. |
| 7,291,165 | B2 | 11/2007 | Rosenthal |
| 7,292,885 | B2 | 11/2007 | Scott |
| 7,300,662 | B2 | 11/2007 | Falotico |
| 7,318,945 | B2 | 1/2008 | Thornton |
| 7,348,319 | B2 | 3/2008 | Hrabie |
| 7,378,106 | B2 | 5/2008 | Hossainy |
| 7,387,641 | B2 | 6/2008 | Schmitt |
| 7,416,559 | B2 | 8/2008 | Shalaby |
| 7,425,218 | B2 | 9/2008 | Keefer |
| 7,438,712 | B2 | 10/2008 | Chouinard |
| 7,445,628 | B2 | 11/2008 | Ragheb |
| 7,491,233 | B1 | 2/2009 | Ding |
| 7,618,448 | B2 | 11/2009 | Schmitz et al. |
| 7,919,162 | B2 | 4/2011 | DeSimone et al. |
| 2004/0044405 | A1 | 3/2004 | Wolff |
| 2005/0142315 | A1 | 6/2005 | DeSimone et al. |
| 2005/0214343 | A1 | 9/2005 | Tremble |
| 2006/0121087 | A1 | 6/2006 | Williams et al. |
| 2007/0026132 | A1 | 2/2007 | Williams et al. |
| 2007/0038284 | A1 | 2/2007 | Williams et al. |
| 2007/0093889 | A1 | 4/2007 | Wu et al. |
| 2007/0123539 | A1 | 5/2007 | Wu |
| 2007/0281250 | A1 | 12/2007 | Aono |
| 2008/0008739 | A1 | 1/2008 | Hossainy et al. |
| 2008/0275539 | A1 | 11/2008 | Williams et al. |
| 2008/0306592 | A1 | 12/2008 | Wang |
| 2009/0216104 | A1 | 8/2009 | DeSimone et al. |

FOREIGN PATENT DOCUMENTS

| | | |
|---|---|---|
| WO | WO9934750 | 7/1999 |

* cited by examiner

POLYMERIC IMPLANT DELIVERY SYSTEM

FIELD OF THE INVENTION

The present invention relates to devices and methods used to deliver polymeric tubular implants to patients in need thereof.

BACKGROUND

A variety of medical conditions are treatable by the implantation of tubular devices into natural body lumens. For example, it is commonplace to implant metallic stents into the coronary arteries of patients with heart disease following balloon angioplasty to minimize the risk that the arteries will undergo restenosis. Recently, commercial stents have included drug-eluting polymer coatings that are designed to further decrease the risk of restenosis. Other examples of conventional tubular medical implants include woven grafts and stent-grafts that are used to span vascular aneurysms, polymeric tubes and catheters that are used to bypass strictures in the ureter and urethra, and stents that are used in the peripheral vasculature, prostate, and esophagus.

Despite the evolution of metallic stents, they continue to have limitations such as the possibility of causing thrombosis and vascular remodeling. While biostable and biodegradable polymeric stents have been proposed to address the limitations of metallic stents, their use has been limited by a number of factors. Among these is the fact that polymeric stents are generally not as strong as their metallic counterparts, and they may undergo stress relaxation if left in a crimped delivery configuration for an extended period of time, such as during shipping and storage. In addition, many conventional stent delivery systems, particularly for self-expanding stents, grasp the stent at isolated locations or otherwise place localized stresses on the stent. For polymeric stents, this presents the possibility that the polymer becomes permanently deformed or otherwise damaged at these localized regions. Moreover, many conventional stent delivery systems do not offer satisfactory control over the movement of a stent as it is released from the delivery system.

There is a need for a delivery system that can be used to deliver polymeric tubular implants, such as stents, into a lumen of a patient without undue risk of damaging the implant during the delivery process. There is also a need for a delivery system that offers the possibility of loading the polymeric tubular implants into the delivery system by a healthcare professional just prior to implantation, thus minimizing the possibility that the implant undergo stress relaxation during shipping and/or storage in a loaded or crimped configuration. There is also a need for a delivery system that releases a tubular implant in a controlled manner.

SUMMARY OF THE INVENTION

In one aspect, the present invention includes delivery systems for the placement of tubular implants within a patient. In another aspect, the present invention includes methods of treating patients by implanting tubular implants using the delivery systems of the present invention. In yet another aspect, the present invention includes kits that include the delivery systems of the present invention.

In one embodiment, the present invention includes a delivery system for the placement of a polymeric tubular implant within a patient. The delivery system includes an inner shaft that comprises a distal end configured for insertion into a patient and a proximal end configured to remain outside of the patient when the distal end is inserted into the patient. At least a portion of the inner shaft has a diameter less than a diameter of the polymeric tubular implant when it is in an unstressed configuration, such that the implant can fit over that portion of the inner shaft. The delivery system includes an expandable member that is slidably disposed about the inner shaft and includes an open distal end that has a cross-sectional dimension that is greater than a diameter of the polymeric tubular implant when the polymeric tubular implant is in an unstressed configuration. As such, the open distal end of the first expandable member is configured for placement therein of at least a portion of the polymeric tubular implant when in an unstressed configuration. The first expandable member includes a proximal end having a cross-sectional dimension that is less than a diameter of the polymeric tubular implant when the polymeric tubular implant is in an unstressed configuration. The delivery system further includes a tubular outer shaft slidably disposed about the inner shaft. The tubular outer shaft has a distal end and a proximal end, wherein the diameter of the tubular outer shaft at its distal end is less than a cross-sectional dimension of the first expandable member at the distal end of the first expandable member, and the diameter of the tubular outer shaft at its distal end is greater than a cross-sectional dimension of the first expandable member at the proximal end of the first expandable member.

DETAILED DESCRIPTION OF THE PREFERRED EMBODIMENTS

The present invention provides devices, methods, and kits used to deliver polymeric tubular implants to patients in need thereof without undue risk of damaging the implant during the delivery process. The tubular implants are generally used for implantation into small diameter bodily lumens, such as those found in the vascular, biliary, uro-genital, gastrointestinal, and tracheal-bronchial anatomy. As is known in the art, such implants are dimensioned according to their intended application and placement location, and are generally several millimeters in diameter, and several millimeters to several tens of millimeters in length. They are formed by any suitable configuration, such as woven strands, loose braids, or unitary frameworks having a repeating or non-repeating pattern, as is known in the art.

Figure 1:
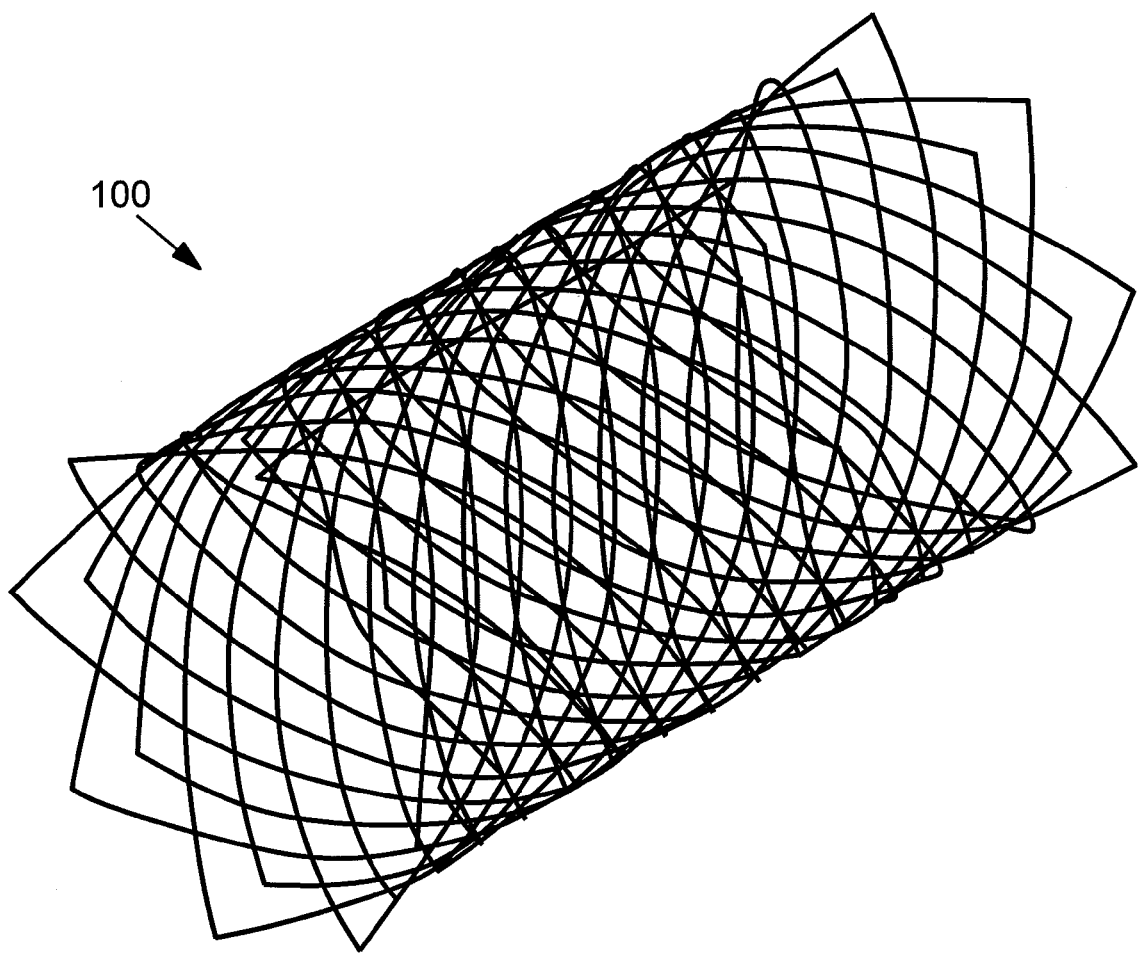
FIG. 1 is a perspective view of a polymeric tubular implant that may be delivered using the delivery system of the present invention.

A representative polymeric tubular implant 100 that may be delivered by the delivery system of the present invention is shown in FIG. 1. The implant 100 is manufactured to have an unstressed configuration, which is characterized by a certain diameter when not acted upon by external stresses. To deliver the implant 100 to a bodily lumen, it is compressed or "crimped" to a reduced diameter, inserted into the lumen using a delivery device, and then released from the delivery device. The implants used with the delivery system of the present invention are "self-expanding" such that when they are released from a delivery device, they will tend to expand towards their unstressed configuration without the aid of expansion means such as an expansion balloon. Preferably, the diameter of the bodily lumen is less than the diameter of the implant in its unstressed configuration so that the self expanding nature of the implant results in the securement of the implant against the lumen wall by a slight pressure.

Figure 2:
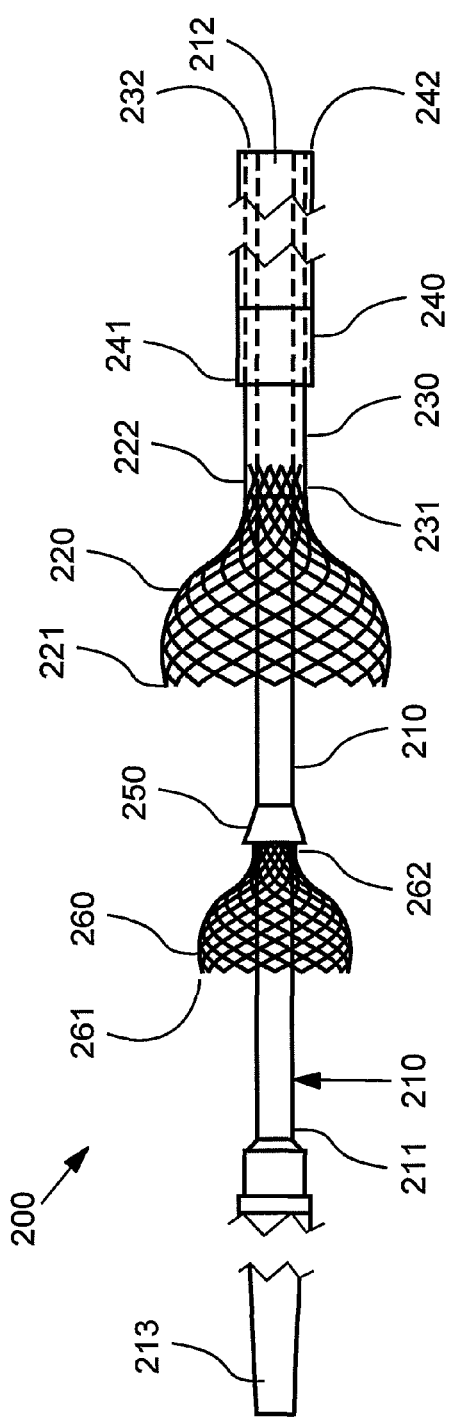
FIG. 2 is a side view of a delivery device, in accordance with an embodiment of the present invention.

An embodiment of the delivery system of the present invention is shown in FIG. 2. Delivery system 200 comprises an inner shaft 210 having distal end 211 configured for insertion into the lumen of a patient and a proximal end 212 configured to remain outside of the patient when the distal end 211 is inserted into the patient. The inner shaft 210 is stiff enough to provide sufficient structural integrity to be pushed through bodily lumens, and is made from any suitable material such as, for example, a biocompatible reinforced or non-reinforced polymer material such as a polyimide, polyamide, high density polyethylene (HDPE), or polyetheretherketone (PEEK). Preferably, a soft tip 213 is connected to the distal end 211 of the inner shaft 210 so to minimize risk of damage to the walls of a bodily lumen during insertion of the delivery system 200. Soft tip 213 is of any suitable shape and is made from any suitable material as is known in the art. Soft tip 213 preferably includes a radiopaque marker or includes a radiopaque filler to enhance visibility under fluoroscopic visualization techniques.

Delivery system 200 includes a first expandable member 220 slidably disposed about the inner shaft 210. In one embodiment, the first expandable member 220 is connected to the distal end 231 of a tubular middle shaft 230, which is slidably disposed about the inner shaft 210 by manipulation of the tubular middle shaft 230 at its proximal end 232. The tubular middle shaft 230 is made from any suitable material that allows it to flex to follow the configuration of the inner shaft 210 as the tubular middle shaft 230 slides over the inner shaft 210. Examples of such materials include, for example, biocompatible reinforced or non-reinforced polymer materials such as polyimides, polyamides, and HDPE.

The first expandable member 220 is a resilient structure that, when not subjected to external stresses, will self-expand to an unstressed configuration such as the configuration shown in FIG. 2. First expandable member 220 may be made from any suitable metallic or polymeric material, and is preferably a shape memory material such as Nitinol. If first expandable member 220 is not made from a shape memory material, it is made from an otherwise elastic material having a configuration that results in a self-expanding property, such as, for example, spring temper stainless steel or cobalt nickel alloys. Preferably, the first expandable member has a mesh or woven structure, as shown in FIG. 2.

Figure 3:
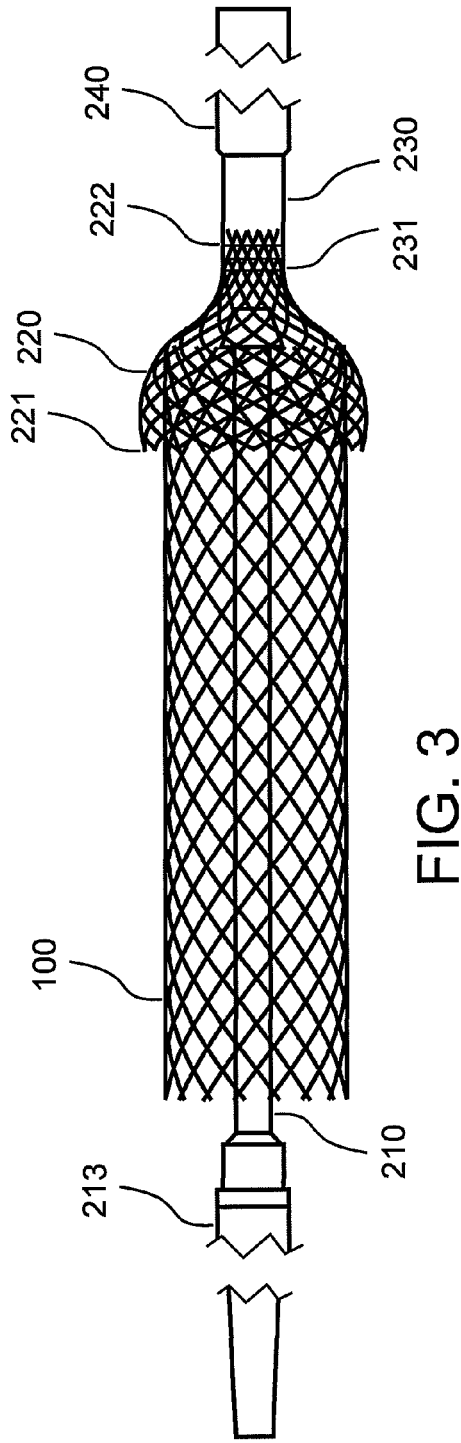
FIG. 3 is a side view of a delivery device during loading of a polymeric tubular implant, in accordance with an embodiment of the present invention.

The first expandable member 220 has an open distal end 221 when in an unstressed configuration. The cross-sectional dimension of the open distal end 221 is greater than the diameter of the implant 100 in its unstressed configuration such that at least a portion of the implant 100 may be placed therein, as shown in FIG. 3. In a preferred embodiment, the proximal end 222 of first expandable member 220 is connected to the distal end 231 of tubular middle shaft 230 using an adhesive or any suitable mechanical attachment means, as previously described. The primary function of the first expandable member 220 is to provide a means of crimping the tubular implant 100 into a reduced configuration to facilitate delivery and placement within a bodily lumen. This action is accomplished by the relative advancement of a tubular outer shaft 240, which is slidably disposed about the inner shaft 210 (and if used, the tubular middle shaft 230), distally such that the tubular outer shaft 240 compresses the first expandable member 220 as it slides over the first expandable member 220. Because at least a portion of the implant 100 is placed within the open distal end 221 of the first expandable member 220, the implant 100 is likewise compressed by the first expandable member 220 as the tubular outer shaft 240 slides over the first expandable member 220. Preferably, and as shown in FIG. 2, the open distal end 221 of first expandable member 220 is circular such that when it compresses the implant 100, it applies a substantially uniform radial force along the circumference of the implant 100 and does not result in the application of any significant stress concentration locations that result in the permanent deformation of the implant 100.

The tubular outer shaft 240 is made from any suitable material that allows it to achieve its intended functions. Preferably, the tubular outer shaft 240 is characterized by a low coefficient of friction to allow for ease of loading and deployment of the implant 100 as described herein. For example, the tubular outer shaft 240 is preferably made from a material such as fluorinated ethylene propylene (FEP) or polytetrafluoroethylene (PTFE), or is coated with a lubricious coating as is known in the art.

The shape of the first expandable member 220 is preferably one that gradually increases from proximal end 222 to distal end 221 so that a gradual compressive force is applied to the implant 100 as the outer shaft 240 is advanced over the first expandable member 220. As shown in FIG. 2, the preferred shape of the first expandable member 220 is similar to a funnel.

Figure 4:
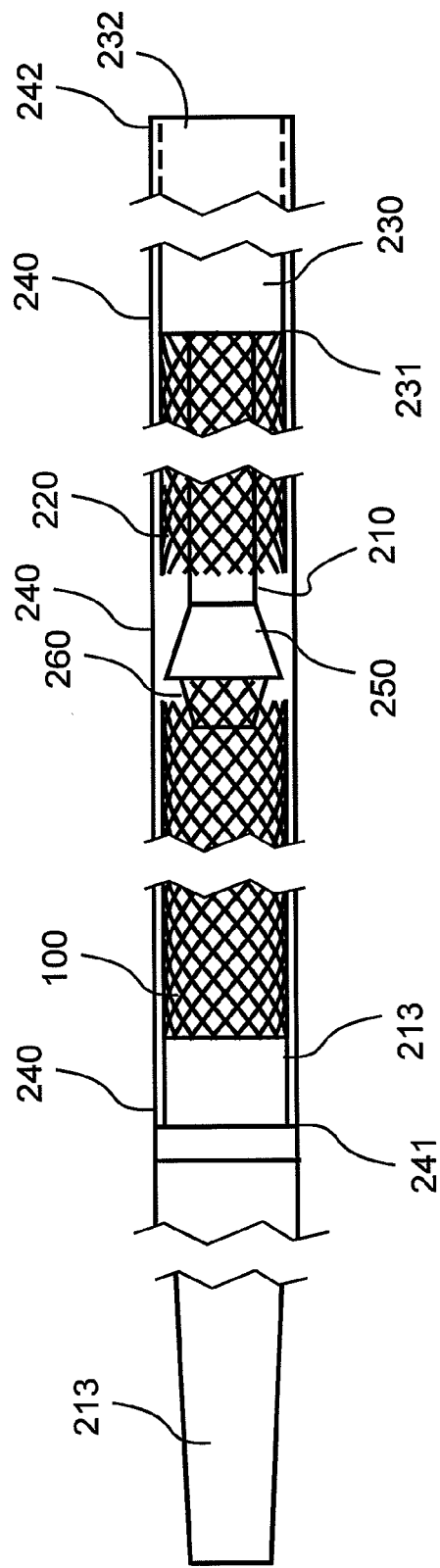
FIG. 4 is a side view of a loaded delivery device, in accordance with an embodiment of the present invention.

To load the delivery system 200 with a polymeric tubular implant 100 outside of a patient's body, the implant 100 (in its unstressed configuration) is advanced over the distal end 211 of the inner shaft 210. In a preferred embodiment, the inner shaft 210 includes an enlarged diameter portion 250 located proximal to the distal end 211. The enlarged diameter portion 250 may be, for example, formed as part of the inner shaft 210 or a ring member or the like that is mounted onto the inner shaft 210. When the enlarged diameter portion 250 is used, the implant 100 is placed between portion 250 and the distal end 211 of the inner shaft 210. When the enlarged diameter portion 250 is not used, the implant 100 is placed at a suitable location along the inner shaft 210 proximal to its distal end 211. The first expandable member 220 is then advanced distally, such as by sliding the tubular middle shaft 230 over the inner shaft 210, so that at least a portion of the implant 100 is located within the open distal end 221 of the first expandable member 220, as shown in FIG. 3. The tubular outer shaft 240 is then advanced distally by sliding it over the inner shaft 210 and/or tubular middle shaft, 230. During the advancement of the tubular outer shaft 240 over the first expandable member 220, the first expandable member 220 applies a radial compressive force to the implant 100, which is crimped into the tubular outer shaft 240 as it is advanced distal to the implant 100 and preferably to the distal end 211 of the inner shaft 210. The tubular outer shaft 240 is advanced to a location at or near the distal end 211 of the inner shaft 210, and if tip 213 is used, the tubular outer shaft 240 is advanced such that it preferably butts against tip 213. The first expandable member 220 is then withdrawn towards the proximal end 212 of the inner shaft 210, such as by withdrawing the tubular middle shaft 230, such that the first expandable member 220 is no longer over any part of the implant 100, as shown in FIG. 4. The use of the enlarged diameter portion 250 may be helpful in withdrawing the first expandable member 220 over the implant 100 when the enlarged diameter portion 250 is sized to function as a stop to prevent the implant from being dragged proximally as the first expandable member 220 is pulled proximally when in contact with the implant 100. Depending upon the materials used for each of the implant 100 and the first expandable member 220, it may also be preferable to apply a lubricious material or coating to the first expandable member 220 to facilitate the ease of withdrawal of the first expandable member 220 over the implant 100.

The delivery system 200 is now ready for insertion into a patient to deliver the implant 100 to a target location. Unlike conventional stent delivery systems that require stent loading as part of the manufacturing and/or packaging processes, the delivery systems of the present invention offers the ability for tubular implants to be loaded by a healthcare professional immediately prior to delivery into a patient. As such, when used with the delivery systems of the present invention and loaded immediately prior to delivery, polymeric implants are not shipped and stored in a crimped configuration and therefore are not likely to undergo stress relaxation. It should be recognized that although the delivery systems of the present invention offer the ability of end-point loading, they are not so limited and may be loaded as part of the manufacturing and/or packaging processes provided that the implant to be delivered is able to withstand shipping and storage while in a crimped configuration and without any adverse effects.

Figure 5:
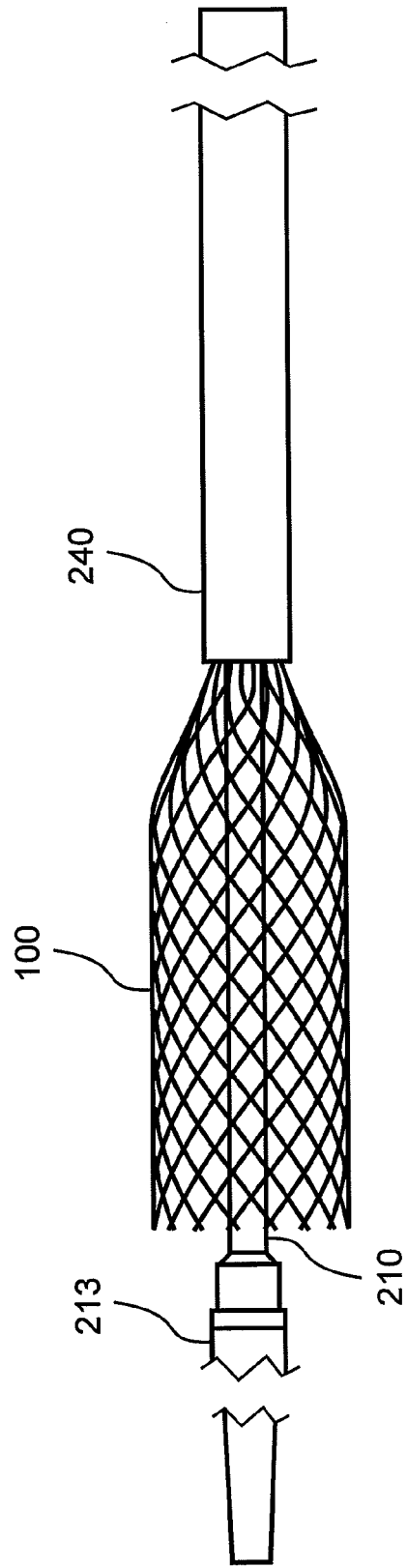
FIG. 5 is a side view of a polymeric tubular implant during delivery using the delivery system of the present invention.

Once the delivery system is advanced to a target location in a patient's body, the outer shaft 240 is then withdrawn in a proximal direction. As the distal end 241 of the outer shaft 240 is withdrawn from over the implant 100, the implant self-expands towards its unstressed configuration as shown in FIG. 5. Once the implant is fully released from its crimped condition, the delivery system 200 is withdrawn from the patient to leave the implant at its desired location.

In an embodiment of the present invention as shown in FIG. 2, the delivery device includes a second expandable member 260 that is affixed to the inner shaft 240 distally from the first expandable member 220. If enlarged diameter portion 250 is used, the second expandable member 260 is located between the enlarged diameter portion 250 and the distal end 211 of the inner shaft 210. Like the first expandable member 220, the distal end 261 of the second expandable member 260 has a cross-sectional diameter greater than the diameter of the polymeric tubular implant 100 when in an unstressed configuration, and a proximal end 262 having a cross-sectional diameter less than the diameter of the polymeric tubular implant 100 when in an unstressed configuration. Unlike the first expandable member 220, however, the second expandable member 260 does not require an open distal end, although in a preferred embodiment, the distal end 261 of second expandable member 260 is open as shown in FIG. 2.

The second expandable member 260 is a resilient structure that, when not subjected to external stresses, will self-expand to an unstressed configuration such as the configuration shown in FIG. 2. Second expandable member 260 may be made from any suitable metallic or polymeric material, and is preferably a shape memory material such as Nitinol. If second expandable member 260 is not made from a shape memory material, it is made from an otherwise elastic material having a configuration that results in a self-expanding property, such as, for example, spring temper stainless steel or cobalt nickel alloys. Preferably, the first expandable member has a mesh or woven structure, as shown in FIG. 2. In other embodiments, the second expandable member 260 is made from a balloon, foam, or other expanding material.

Figure 6:
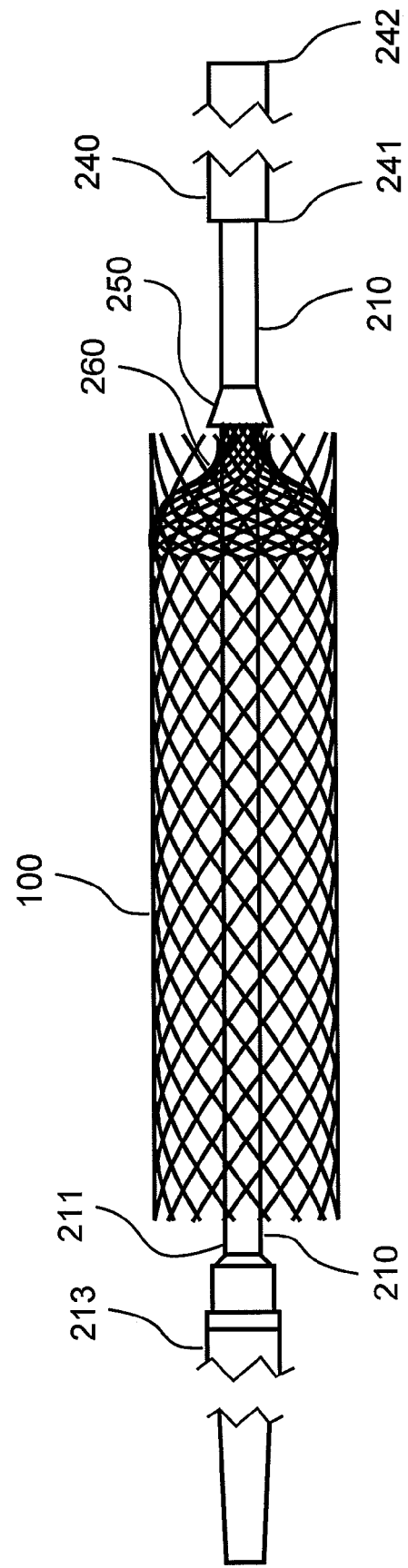
FIG. 6 is a side view of a delivery device during loading of a polymeric tubular implant, in accordance with an embodiment of the present invention.

In use, the implant is placed over the second expandable member 260 prior to crimping, as shown in FIG. 6. When the implant is crimped using the first expandable member 220 and the tubular outer shaft 240, the second expandable member 260 is likewise compressed to a reduced configuration beneath the implant 100, as shown in FIG. 4. Likewise, the second expandable member 260 expands with the polymeric tubular implant 100 when it is released from its crimped configuration. Because the distal end 261 of the second expandable member 260 has a cross-sectional diameter greater than the diameter of the polymeric tubular implant 100 when in an unstressed configuration, the second expandable member 260 applies a force to the inner diameter of the implant 100. This force may help the implant 100 to expand to its desired configuration, and will further prevent a sometimes-occurring phenomenon known as "stent jumping" in which self-expanding implants excessively move or "jump" when they are extruded from their delivery devices. Use of the second expandable member 260 therefore results in an improvement in the controlled delivery of implant 100 when compared with conventional delivery devices of self-expanding medical implants.

When enlarged diameter portion 250 and second expandable member 260 are used with the present invention, the proximal end 261 of the second expandable member 260 preferably has a cross-sectional diameter that is less than that of the enlarged diameter portion 250 so that the enlarged diameter portion 250 can fulfill its intended purpose, as previously described, to prevent the implant from being dragged proximally as the first expandable member 220 is pulled proximally when in contact with the implant 100.

The present invention includes kits that include the delivery system 200 or the components thereof. In one embodiment, the kit includes an inner shaft 210, a tubular middle shaft having a first expandable member 220 attached thereto, and a tubular outer shaft 240, which may be packaged as separate components or pre-assembled as described herein. An implant 100 may be kitted in the same packaging with the delivery system 200, or may be provided separately.

Figure 7A:
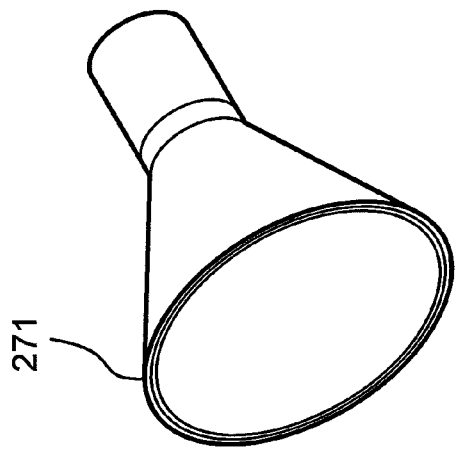
FIGS. 7a and 7b show an optional funnel for use with the delivery system of the present invention.
Figure 7B:
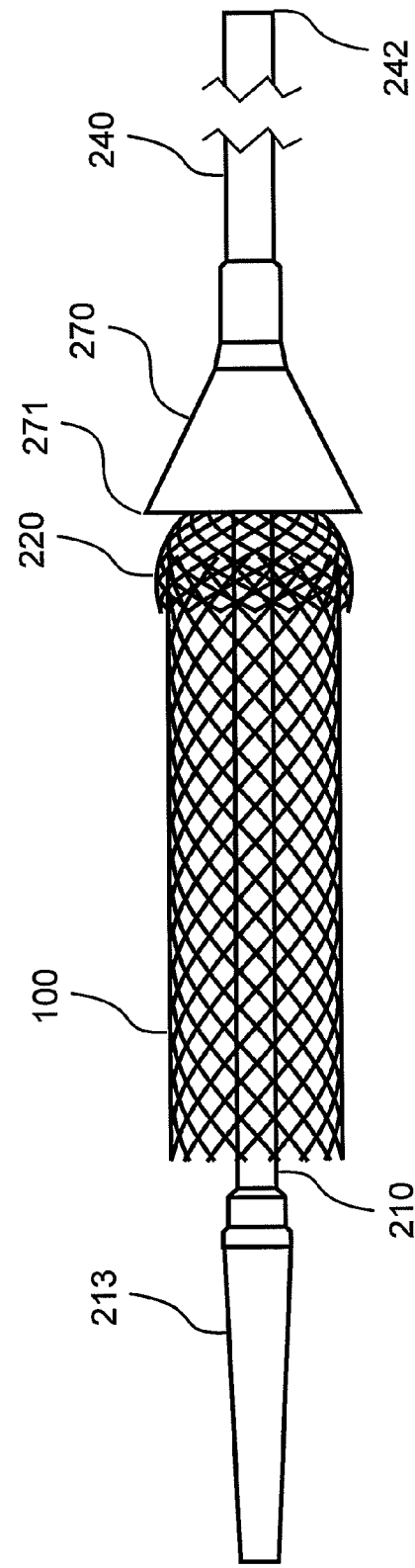

The kit of the present invention may also include an optional funnel 270 which is detachably connectable to the distal end of the tubular outer shaft 240 as shown in FIGS. 7a and 7b. Funnel 270 is made from any suitable material, and is preferably a low friction material such as FEP or PTFE. The cross-sectional dimension of distal end 271 of funnel 270 is greater than the diameter of the implant 100 in its unstressed configuration. During loading of the implant 100 into the delivery system 200, funnel 270 may be useful in drawing the first expandable member 220 and implant 100 to within the tubular outer shaft 240. To achieve this purpose, funnel 270 is placed over the proximal end 242 of the outer shaft 240 and advanced to the distal end 241, the outer shaft 240 is moved relative to the tubular middle shaft 230, the inner shaft 210, and the implant 100 to place the first expandable member 220 and implant 100 within the tubular outer shaft 240, and the funnel 270 is then removed from the outer shaft 240 by sliding over either of its distal or proximal ends 241, 242.

The present invention provides devices, methods, and kits used to deliver polymeric tubular implants to patients in need thereof without undue risk of damaging the implant during the delivery process. While aspects of the invention have been described with reference to example embodiments thereof, it will be understood by those skilled in the art that various changes in form and details may be made therein without departing from the scope of the invention.

We claim:

1. A delivery system for the placement of a tubular implant within a patient, comprising:
a tubular implant having a first diameter when in an unstressed configuration and a second diameter less than the first diameter when in a compressed configuration; and
a delivery device, comprising:
an inner shaft comprising a distal end configured for insertion into a patient and a proximal end configured to remain outside of the patient when the distal end is inserted into the patient, at least a portion of said inner shaft having a diameter less than the first diameter of the tubular implant when the tubular implant is in an unstressed configuration;
a first expandable member slidably disposed about said inner shaft, said first expandable member comprising an open distal end having a cross-sectional dimension greater than the first diameter of the tubular implant the open distal end of said first expandable member configured for placement therein of at least a portion of the tubular implant when in an unstressed configuration, said first expandable member comprising a proximal end having a cross-sectional dimension less than the first diameter of the tubular implant when the tubular implant is in an unstressed configuration;
a second expandable member affixed to said inner shaft said second expandable member comprising an open distal end; and
a tubular outer shaft slidably disposed about said inner shaft, said tubular outer shaft having a distal end and a proximal end, wherein the diameter of said tubular outer shaft at its distal end is less than a cross-sectional dimension of said first expandable member at the distal end of said first expandable member, and the diameter of said tubular outer shaft at its distal end is greater than a cross-sectional dimension of said first expandable member at the proximal end of said first expandable member;
wherein the tubular implant is removably disposed between the inner shaft and the tubular outer shaft and between the first and second expandable members;
wherein each of the first and second expandable members consists of a material selected from the group consisting of mesh material and woven material.

2. The delivery system of claim 1, further comprising a polymeric tip connected to the distal end of said inner shaft.

3. The delivery system of claim 1, further comprising a tubular middle shaft slidably disposed about said inner shaft and located between said inner shaft and said tubular outer shaft.

4. The delivery system of claim 3, wherein the proximal end of said first expandable member is connected to said tubular middle shaft.

5. The delivery system of claim 4, wherein said first expandable member is connected to said tubular middle shaft with an adhesive.

6. The delivery system of claim 1, wherein said first expandable member is funnel-shaped when expanded.

7. The delivery system of claim 1, wherein said open distal end of said second expandable member has a cross-sectional dimension greater than the first diameter of the tubular implant when the tubular implant is in an unstressed configuration, and said second expandable member has a proximal end having a cross-sectional dimension less than the first diameter of the tubular implant when the tubular implant is in an unstressed configuration, said second expandable member being configured to be at least partially placed inside of the tubular implant.

8. The delivery system of claim 1, wherein said inner shaft comprises an enlarged diameter portion, the enlarged diameter portion being located proximal to the second expandable member and the distal end of said inner shaft and distal to the first expandable member.

9. The delivery system of claim 1, further comprising a funnel removably attached to the distal end of said tubular outer shaft.

10. A kit comprising the delivery system of claim 1.

11. A delivery system for a tubular, the delivery system comprising:
an inner shaft comprising a distal end configured for insertion into a patient and a proximal end configured to remain outside of the patient when the distal end is inserted into the patient, at least a portion of said inner shaft having a diameter less than the first diameter of the tubular implant when the tubular implant is in an unstressed configuration;
a soft tip disposed at a distal-most end of the inner shaft;
a tubular middle shaft slidably disposed about said inner shaft, said tubular middle shaft comprising a distal end and a proximal end;
a first expandable member connected to the distal end of said tubular middle shaft, said first expandable member comprising an open distal end having a cross-sectional dimension greater than the first diameter of the tubular implant when the tubular implant is in an unstressed configuration, the open distal end of said first expandable member configured for placement therein of at least a portion of the tubular implant when in an unstressed configuration, said first expandable member comprising a proximal end having a cross-sectional dimension less than the first diameter of the tubular implant when the tubular implant is in an unstressed configuration;
a second expandable member affixed to said inner shaft said second expandable member comprising an open distal end;
a tubular outer shaft slidably disposed about said inner shaft, said tubular outer shaft having a distal end and a proximal end, wherein the diameter of said tubular outer shaft at its distal end is less than a cross-sectional dimension of said first expandable member at the distal end of said first expandable member, and the diameter of said tubular outer shaft at its distal end is greater than a cross-sectional dimension of said first expandable member at the proximal end of said first expandable member; and
a tubular implant having a first diameter when the implant is in an unstressed configuration and a second diameter less than the first diameter when the implant is in a compressed configuration, wherein said tubular implant is removably disposed between the inner shaft and the tubular outer shaft and between the first and second expandable members.

* * * * *

UNITED STATES PATENT AND TRADEMARK OFFICE
CERTIFICATE OF CORRECTION

PATENT NO.         : 8,372,133 B2                                      Page 1 of 1
APPLICATION NO.    : 12/573687
DATED              : February 12, 2013
INVENTOR(S)        : Nareak Douk et al.

It is certified that error appears in the above-identified patent and that said Letters Patent is hereby corrected as shown below:

In the Claims:

Column 8, Claim 11, line 17, should read:

- A delivery system for a tubular implant, -

Signed and Sealed this
Twenty-fifth Day of February, 2014

Michelle K. Lee
*Deputy Director of the United States Patent and Trademark Office*